(12) United States Patent
Jones et al.

(10) Patent No.: US 8,273,127 B2
(45) Date of Patent: Sep. 25, 2012

(54) INTERBODY FUSION DEVICE AND ASSOCIATED METHODS

(75) Inventors: Robert J. Jones, Austin, TX (US); Kevin Dunworth, Dripping Springs, TX (US)

(73) Assignee: SpineSmith Partners, L.P., Austin, TX (US)

( * ) Notice: Subject to any disclaimer, the term of this patent is extended or adjusted under 35 U.S.C. 154(b) by 1476 days.

(21) Appl. No.: 11/759,219

(22) Filed: Jun. 6, 2007

(65) Prior Publication Data

US 2008/0306596 A1    Dec. 11, 2008

(51) Int. Cl.
*A61F 2/44* (2006.01)

(52) U.S. Cl. .................................... 623/17.16

(58) Field of Classification Search .......... 606/246–249, 606/90, 105; 623/17.11
See application file for complete search history.

(56) References Cited

U.S. PATENT DOCUMENTS

| | | | |
|---|---|---|---|
| 4,904,261 A | 2/1990 | Dove et al. | |
| 4,955,908 A | 9/1990 | Frey et al. | |
| 5,397,364 A * | 3/1995 | Kozak et al. | 623/17.11 |
| 5,861,041 A | 1/1999 | Tienboon | |
| 6,066,175 A | 5/2000 | Henderson et al. | |
| 6,235,034 B1 * | 5/2001 | Bray | 606/71 |
| 6,241,769 B1 | 6/2001 | Nicholson et al. | |
| 6,258,125 B1 | 7/2001 | Paul et al. | |
| 6,432,106 B1 | 8/2002 | Fraser | |
| 6,468,311 B2 * | 10/2002 | Boyd et al. | 623/17.16 |
| 6,558,424 B2 | 5/2003 | Thalgott | |
| 6,579,290 B1 | 6/2003 | Hardcastle et al. | |
| 6,635,060 B2 | 10/2003 | Hanson et al. | |
| 6,706,067 B2 | 3/2004 | Shimp et al. | |
| 6,953,477 B2 | 10/2005 | Berry | |
| 6,972,019 B2 | 12/2005 | Michelson | |
| 6,989,031 B2 | 1/2006 | Michelson | |
| 7,018,412 B2 | 3/2006 | Ferreira et al. | |
| 7,018,414 B2 | 3/2006 | Brau et al. | |
| 7,018,416 B2 | 3/2006 | Hanson et al. | |
| 7,033,394 B2 | 4/2006 | Michelson | |
| D530,423 S | 10/2006 | Miles et al. | |
| 7,125,424 B2 | 10/2006 | Banick et al. | |
| 7,135,043 B2 | 11/2006 | Nakahara et al. | |
| 7,172,627 B2 | 2/2007 | Fiere et al. | |

(Continued)

FOREIGN PATENT DOCUMENTS

EP    1103236    5/2001

(Continued)

OTHER PUBLICATIONS

SynFix-LR Technique Guide, Synthes GmbH, copyright 2006.

*Primary Examiner* — Eduardo C Robert
*Assistant Examiner* — Tara Carter
(74) *Attorney, Agent, or Firm* — Winstead PC

(57) ABSTRACT

A method and apparatus is provided for use in spinal fusion procedures. An interbody fusion device has a first piece that is a load bearing device designed to bear the axial loading from the end plates of adjacent vertebrae. A second piece of the interbody fusion device is a retention device whose function is to prevent migration of the load bearing device. One or more fasteners secure the retention device to the vertebrae above and below the load bearing device. The fasteners cause the end plates of the vertebrae to compress the end plates to the load bearing device to facilitate proper fusion.

11 Claims, 6 Drawing Sheets

U.S. PATENT DOCUMENTS

| | | |
|---|---|---|
| 7,674,297 B2 | 3/2010 | Falahee |
| 2002/0138146 A1 | 9/2002 | Jackson ............... 623/17.15 |
| 2002/0161445 A1 | 10/2002 | Crozet |
| 2004/0034430 A1 | 2/2004 | Falahee |
| 2005/0101960 A1 | 5/2005 | Fiere et al. |
| 2005/0143819 A1 | 6/2005 | Falahee |
| 2006/0085071 A1 | 4/2006 | Lechmann ............ 623/17.11 |
| 2006/0173543 A1 | 8/2006 | Brau et al. |
| 2007/0250167 A1 | 10/2007 | Bray et al. |
| 2008/0306596 A1 | 12/2008 | Jones et al. |
| 2009/0105830 A1 | 4/2009 | Jones et al. |
| 2009/0105831 A1 | 4/2009 | Jones et al. |

FOREIGN PATENT DOCUMENTS

| | | |
|---|---|---|
| EP | 1847240 | 10/2007 |
| WO | WO 2007098288 | 8/2007 |

* cited by examiner

INTERBODY FUSION DEVICE AND ASSOCIATED METHODS

FIELD OF THE INVENTION

This invention relates to the field of spinal fusion. In particular, this invention is drawn to spinal fusion devices and associated methods.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

One problem with prior art spinal fusion techniques relates to device migration. For example, prior to complete bone fusion, a fusion device may migrate from the desired position. In examples where bone screws are used, the insertion and tightening of the bone screws tends to cause device migration. Another problem with typical prior art fusion techniques is that fusion devices, or associated plates or fasteners, protrude from the spine, causing discomfort, damage, or danger to surrounding vascular or neurological tissues.

There is therefore a need for spinal fusion devices and related spinal fusion procedures that adequately treats degenerative disc disease and other spinal conditions, while providing improvements over the prior art.

SUMMARY OF THE INVENTION

An apparatus of the invention provides a spinal fusion device including a fusion bearing device configured to fit between two adjacent vertebrae, and a retention device configured to be secured to at least one of the adjacent vertebrae to prevent migration of the fusion bearing device, wherein the retention device has a height that is less than the height of the fusion bearing device.

One embodiment of an interbody fusion device includes a first piece configured to be placed between adjacent vertebrae, a second piece configured to at least partially fit within the first piece when the first piece is inserted between adjacent vertebrae, and one or more fastening devices for securing the second piece to at least one of the adjacent vertebrae.

Another embodiment of the invention provides a spinal fusion device including a fusion bearing device configured to fit between two adjacent vertebrae, a retention device configured to prevent migration of the fusion bearing device, wherein the retention device has a height that is less than the height of the fusion bearing device, one or more fasteners coupled to the retention device to compress the two adjacent vertebrae to the fusion bearing device.

Another embodiment of the invention provides a method of fusing adjacent vertebrae including providing an interbody fusion device, inserting the interbody fusion device between two adjacent vertebrae, providing a retention device configured to fit within the interbody fusion device, sliding the retention device into the interbody fusion device, and securing the retention device to at least one of the adjacent vertebrae.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

The present invention relates to spinal fusion implants and related spinal fusion procedures for use in cervical and lumbar applications. One type of spinal fusion is interbody fusion. Typically, an interbody fusion procedure places a bone graft between the vertebra in the area normally occupied by an intervertebral disc. In preparation for a spinal fusion procedure, the intervertebral disc is removed entirely. A device may be placed between the vertebra to maintain spine alignment and disc height. Fusion then occurs between the endplates of the vertebrae. In some examples, fusion is augmented by a process called fixation, meaning the placement of screws, rods or plates to stabilize the vertebra to facilitate bone fusion. The present invention provides an interbody fusion device that overcomes problems found in the prior art.

Generally, the present invention provides a two piece interbody fusion device that may be used with anterior lumbar interbody fusion (ALIF). In one example, a first piece of the interbody fusion device is a U-shaped load bearing device that is designed to bear the axial loading from the end plates of adjacent vertebrae. A second piece of the interbody fusion device is a retention device whose function is to prevent migration of the load bearing device. One or more fasteners, such as bone screws secure the retention device to the vertebrae above and below the load bearing device. The fasteners cause the end plates of the vertebrae to compress the end plates to the load bearing device to facilitate proper fusion. If desired, the fasteners may include an anti-backout mechanism.

Figure 1:
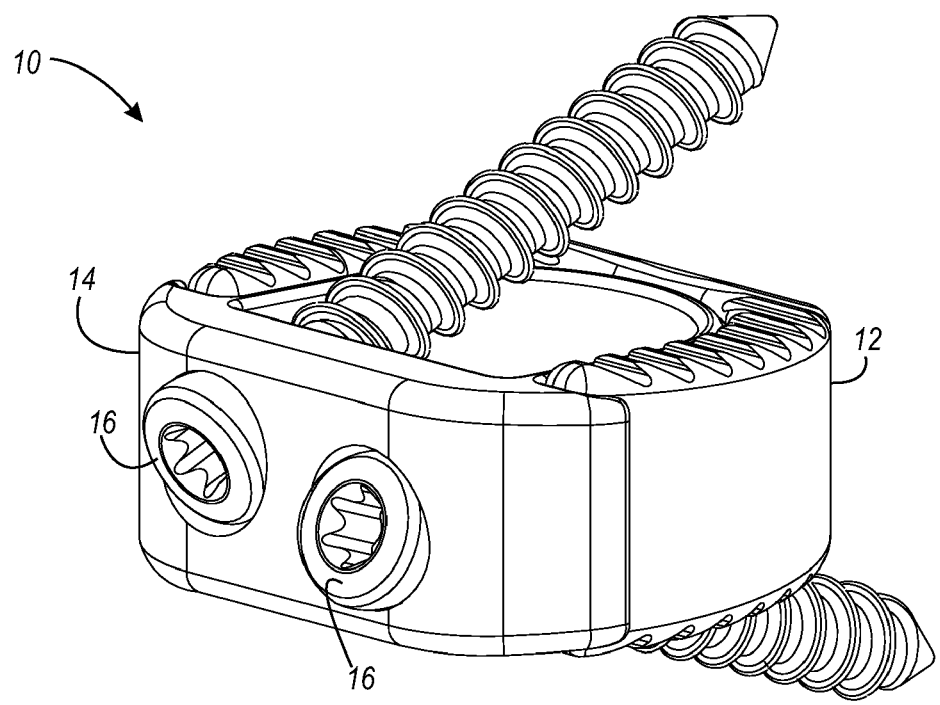
FIG. 1 is an isometric view of one example of an interbody fusion device of the present invention.

FIG. 1 is an isometric view of one example of an interbody fusion device of the present invention. FIG. 1 shows an interbody fusion device 10. The interbody fusion device 10 includes a load bearing device 12, a retention device 14, and two bone screws 16, each of which are described in more detail below.

Figure 2:
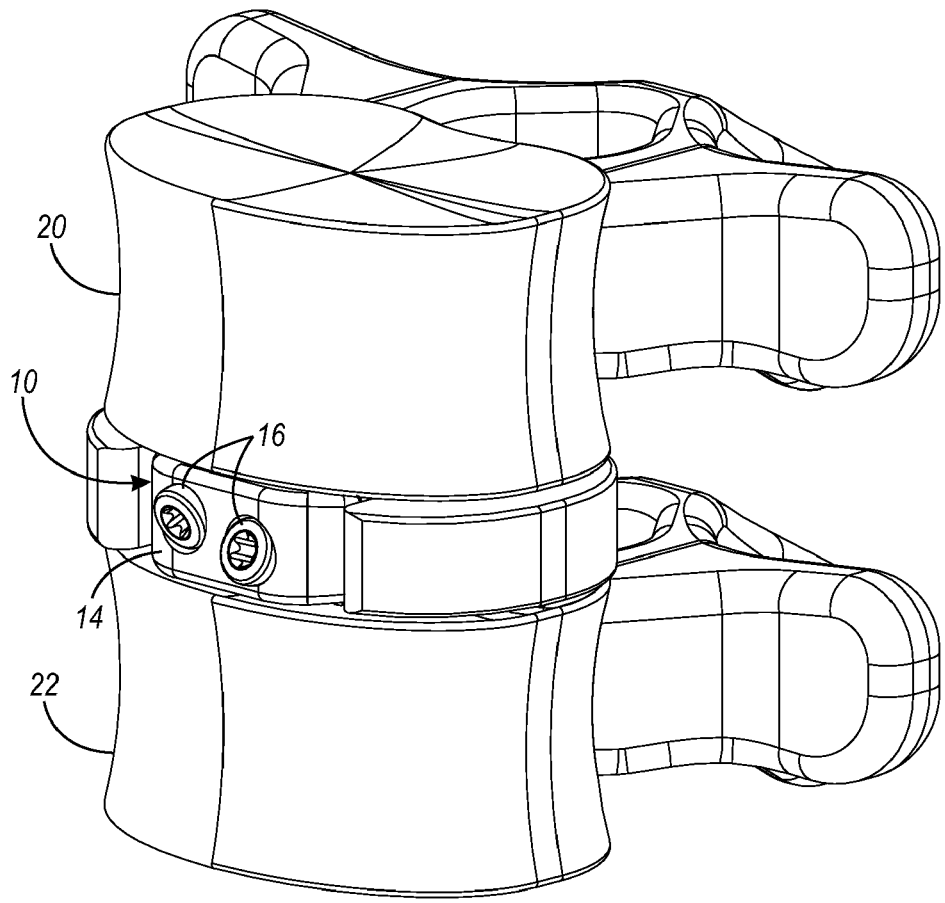
FIG. 2 is an isometric diagram of the interbody fusion device shown in FIG. 1 installed between the end plates of two adjacent vertebrae.

FIG. 2 is an isometric diagram of the interbody fusion device 10 shown in FIG. 1 installed between the end plates of two adjacent vertebrae 20 and 22 to facilitate the fusion of the vertebrae 20 and 22. The interbody fusion device 10 provides load bearing support as well as the proper spacing between the vertebrae 20 and 22 while fusion of the vertebrae takes place. As described in more detail below, the interbody fusion device 10 is positioned between the end plates of the vertebrae 20 and 22 within the vertebral body in the area usually occupied by the intervertebral disc.

Figure 3:
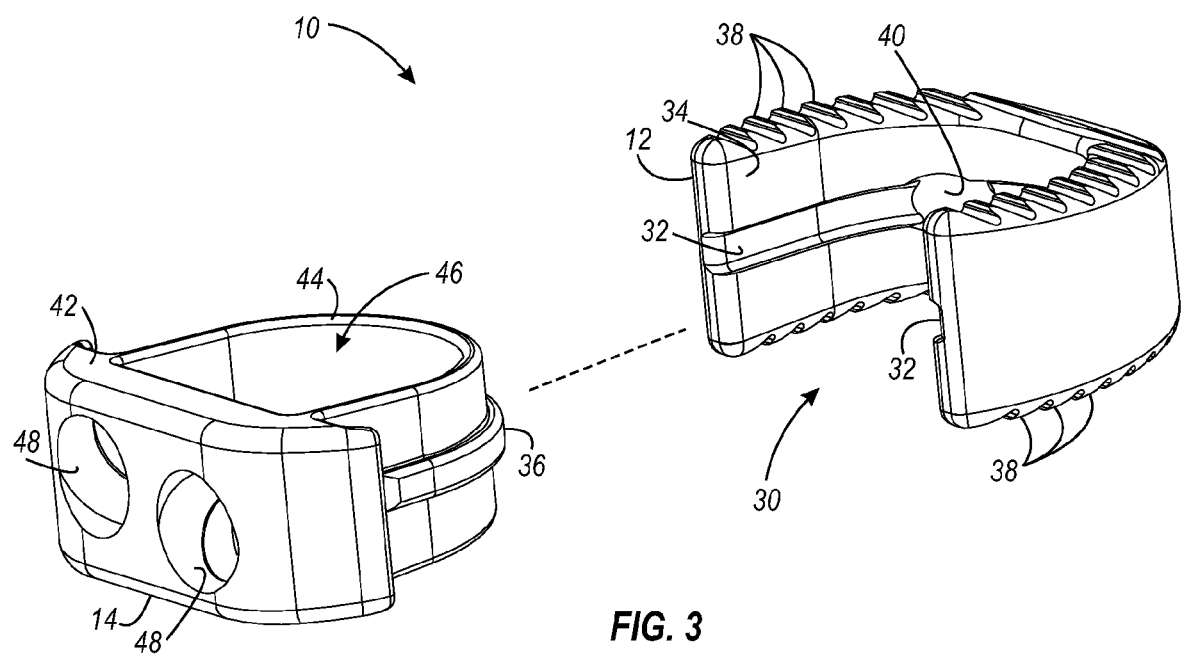
FIG. 3 is an exploded view of an interbody fusion device, showing a load bearing device and a retention device.

FIGS. 3-6 are views illustrating various details of one example of an interbody fusion device of the present invention. FIG. 3 is an exploded view of the interbody fusion device 10, showing the load bearing device 12 and the retention device 14 separately. The load bearing device 12 is a generally U-shaped device having an open end 30 that is configured to receive the retention device 14 (described below). A groove 32 is formed around the interior surface 34 of the load bearing device 12. A corresponding tongue 36 is formed around the outside surface of the retention device 14 such that, when the retention device 14 is inserted within the open end 30 of the load bearing device 12, the tongue 36 and groove 32 tend to hold the retention device 14 in a desired position, relative to the load bearing device 12.

The load bearing device 12 also includes a plurality of ridges 38 formed on the top and bottom ends of the device 12. The ridges 38 are angled and come to a point in such a way that the ridges 38 help to hold the load bearing device 12 to the end plates of the vertebrae to reduce the chance of anterior migration of the implant. If desired, one or more openings 40 can be formed in the load bearing device 12 to facilitate instrumentation devices. In the example shown in FIG. 3, two openings 40 are formed on opposite sides of the load bearing device 12 (the second opening 40 is hidden in FIG. 3). An implant holder can be used to insert the load bearing device 12 into a vertebral body using the openings 40.

The retention device 14 has a front portion 42 and a rear portion 44 that, together, form a hollow body 46. The hollow body 46 provides a relatively large graft volume, compared to a typical ALIF allograft. Prior to insertion into the load bearing device 12, the hollow body 46 of the retention device 14 can be filled with a prepared material that will help to facilitate fusion of the vertebrae (see FIGS. 9-10). Examples of a material include allograft bone, bone marrow, bone morphonogenic protein (BMP), Autologous Stem Cells, etc., to facilitate fusion through opening 46.

The retention device 14 is shaped to such that it will fit within the open end 30 of the load bearing device 12. In the example shown in FIG. 3, two holes 48 are formed in the front portion 42, and are adapted to received fasteners, such as bone screws, pegs, etc. One of the holes 48 is angled down, and the other hole 48 is angled up, such that a first fastener can be secured to the vertebra above the interbody fusion device 10, and a second fastener can be secured to the vertebra below the interbody fusion device 10 (described in more detail below).

Figure 4:
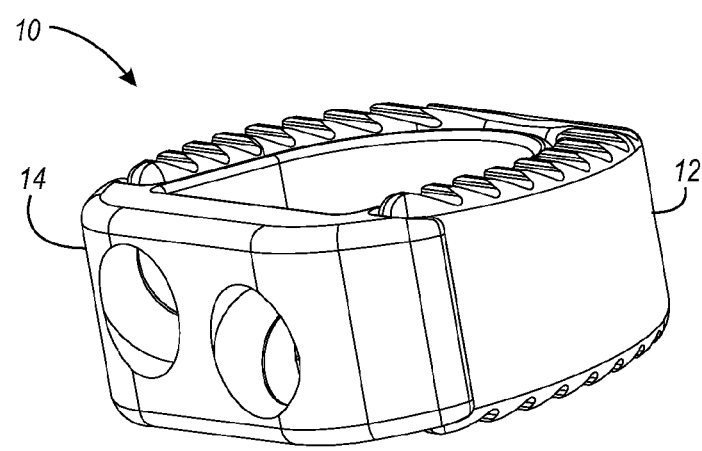
FIG. 4 is an isometric diagram of the interbody fusion device shown in FIG. 3 with the retention device inserted into the load bearing device.

FIG. 4 is an isometric diagram of the interbody fusion device 10 shown in FIG. 3 with the retention device 14 inserted into the load bearing device 12. As shown, the retention device 14 fits within the load bearing device 12. The resulting assembly provides a load bearing structure that is safely secured in place without any fasteners having to be placed directly into the load bearing device 12. FIG. 4 also illustrates that the height of the retention device 14 is less than the height of the load bearing device 12. As a result, all of the load on the vertebrae will be placed on the load bearing device 12, and not on the retention device 14. At the same time the load bearing device 12 is securely is the position desired by the surgeon. In some prior art devices, the fastening mechanisms (e.g., cervical plates with screws, spacers held in place by off-set screws, etc.), will bear some of the load, increasing the likelihood of device failure or migration. In addition, with typical prior art devices, a spacer is likely to migrate or twist slightly as bone screws are tightened by the surgeon. With the interbody fusion device 10 of the present invention, the load bearing structure will remain stationary, even as bone screws are tightened to secure the retention device in place.

Figure 5:
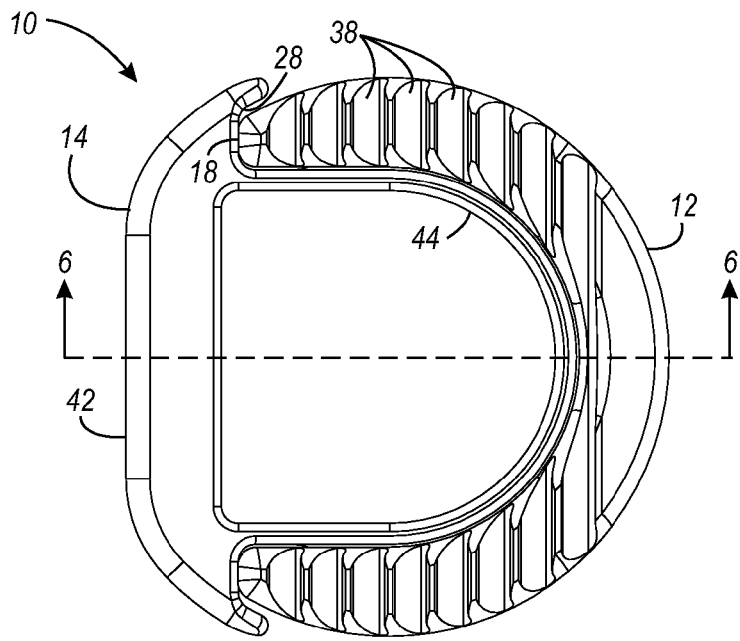
FIG. 5 is a top view of the assembled interbody fusion device shown in FIG. 4.

FIG. 5 is a top view of the assembled interbody fusion device 10 shown in FIG. 4. As shown, when the load bearing device 12 and retention device 14 are put together, the interbody fusion device 10 has a generally round profile, that substantially fits within a vertebral body (shown in more detail below). FIG. 5 also illustrates how the load bearing device 12 is securely held in place by the retention device 14, such that anterior and lateral migration is prevented. Also note that that trailing edges 18 of the load bearing device 12 are nested and contained in pockets 28 formed in the retention device 14. This further secures the load bearing device 12 in place.

Figure 6:
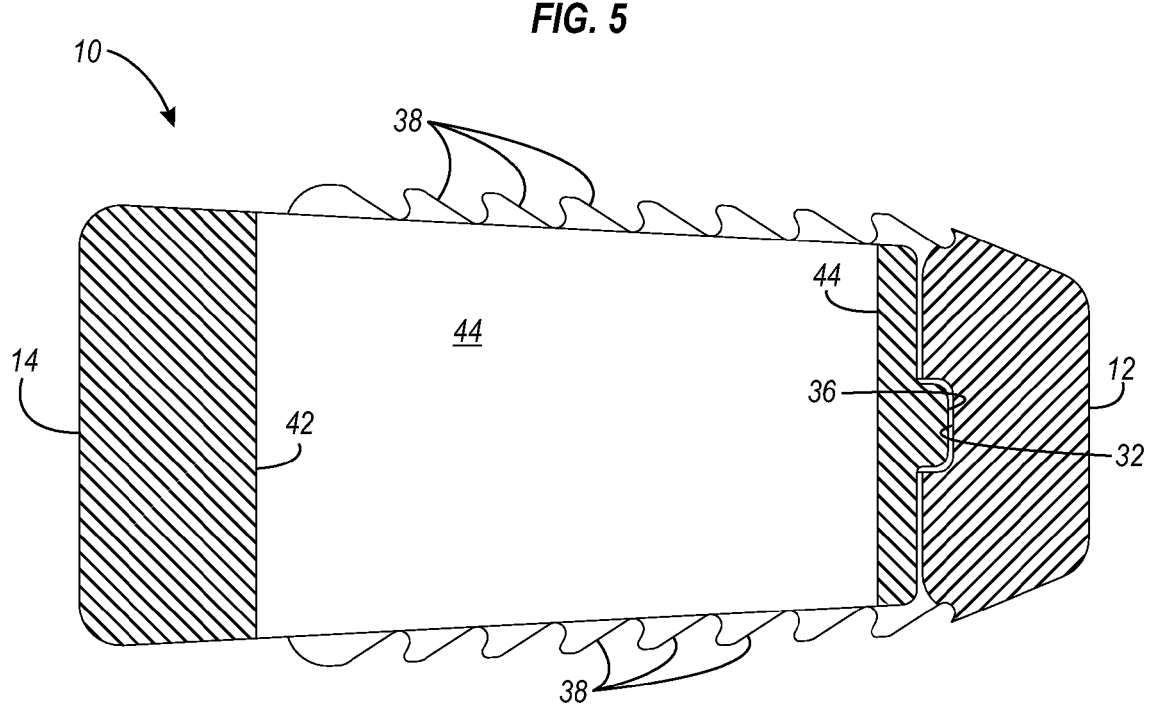
FIG. 6 is a sectional diagram taken along line 6-6 of FIG. 5.

FIG. 6 is a sectional diagram taken along line 6-6 of FIG. 5. FIG. 6 shows the retention device 14, including the front portion 42 and the rear portion 44, which forms the hollow body 46. The tongue 36 of the retention device 14 fits within the groove 32 of the load bearing device 12. FIG. 6 also more clearly illustrates that the height of the load bearing device 12 is greater than the height of the retention device 14. As a result, the load bearing device 12 will be the structure (primarily, the ridges 38) that engages the end plates of the vertebrae, thus supporting the axial loading of the vertebrae.

Figure 7:
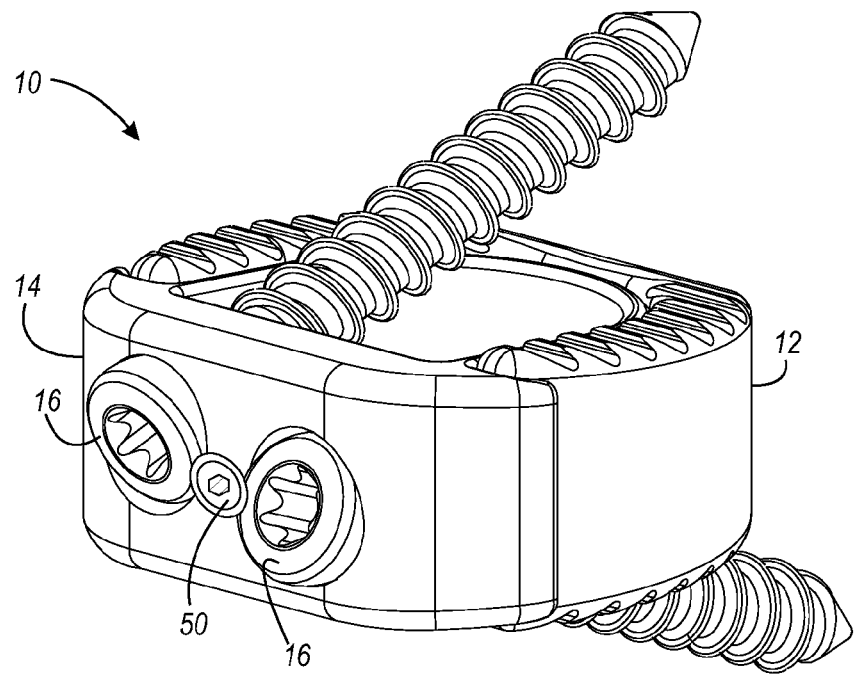
FIG. 7 is an isometric diagram of an interbody fusion device utilizing an anti-backout mechanism.

As mentioned above, the bone screws 16 may include an anti-backout mechanism. FIG. 7 is an isometric diagram of the interbody fusion device 10 utilizing an anti-backout mechanism. In this example, the anti-backout mechanism is comprised of a set screw 50, which can be screwed into the front portion of the retention device 14. The set screw in this example includes a driver socket for receiving a driver, which may be used by a surgeon to tighten the set screw 50. Of course, any desired type of anti-backout device may also be used.

As was shown in FIG. 2, a interbody fusion device of the present invention is intended to be installed between the end plates of two adjacent vertebrae to facilitate the fusion of the vertebrae. FIGS. 8-11 further illustrate the installation of an interbody fusion device of the present invention between adjacent vertebrae.

Figure 8:
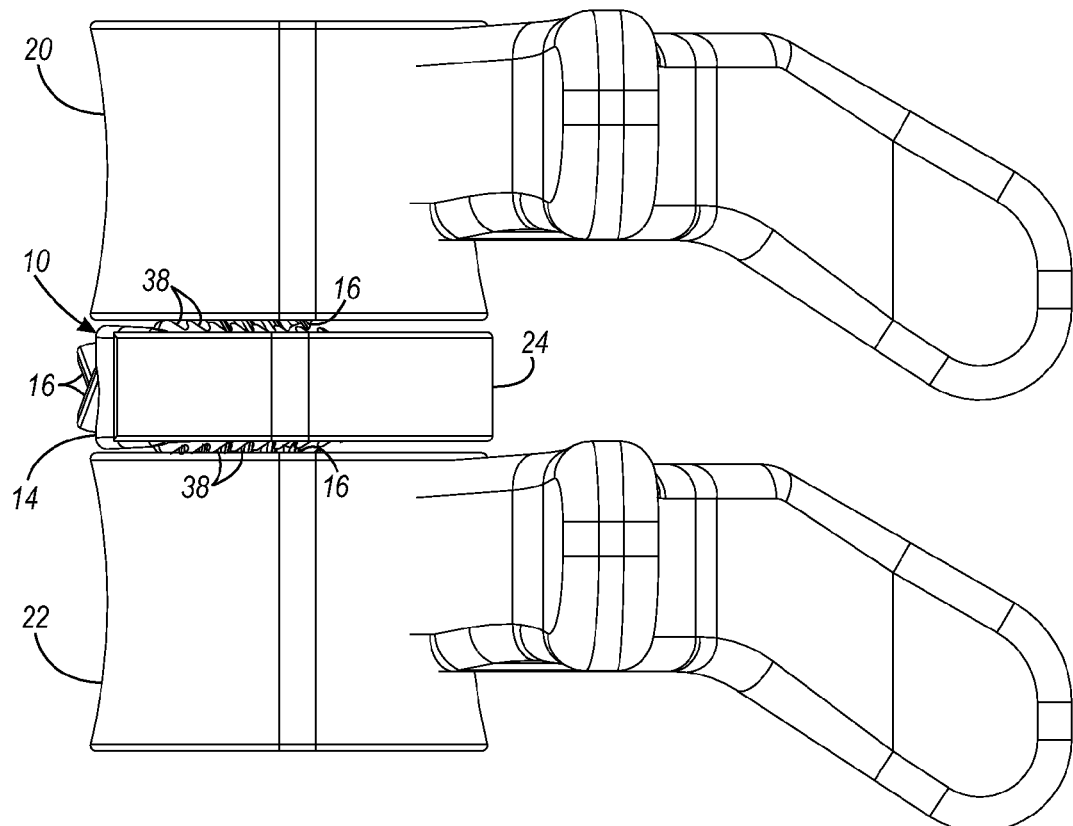
FIG. 8 is a side view of the interbody fusion device and vertebrae shown in FIG. 2.

FIG. 8 is a side view of the interbody fusion device 10 and vertebrae shown in FIG. 2. As shown in FIG. 8, the interbody fusion device 10 has a zero-profile anteriorly. In other words, the interbody fusion device 10 has a shape (e.g., see FIG. 5) in the axial plane that substantially fits within the perimeter defined by the vertebrae. In typical prior art devices, a cervical plate, or similar structure, is affixed to the side of the vertebrae, creating an extending profile that can cause discomfort, or damage to nearby tissue. Also note from FIG. 8 that the interbody fusion device 10 (not including the bone screws 16) also does not extend beyond (above or below) the end plates of the vertebrae.

Prior to the insertion of the interbody fusion device 10, the intervertebral disc is removed, so the interbody fusion device 10 can be place between the vertebrae 20 and 22. In one example, a window is cut in the disc annulus 24. Next, portions of the nucleus pulposus 26 (FIGS. 9, 10) are removed so that the interbody fusion device 10 can fit between the vertebrae 20 and 22 as shown in the figures.

Figure 9:
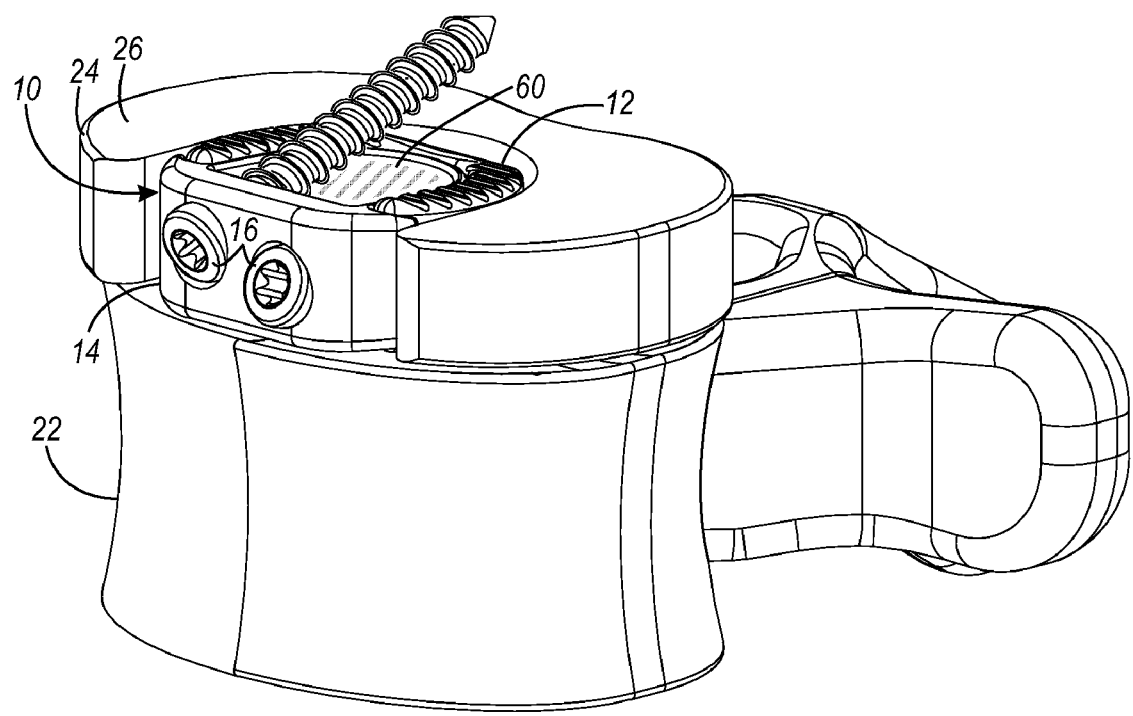
FIG. 9 is an isometric view similar to FIG. 2, but with the upper vertebra removed.
Figure 10:
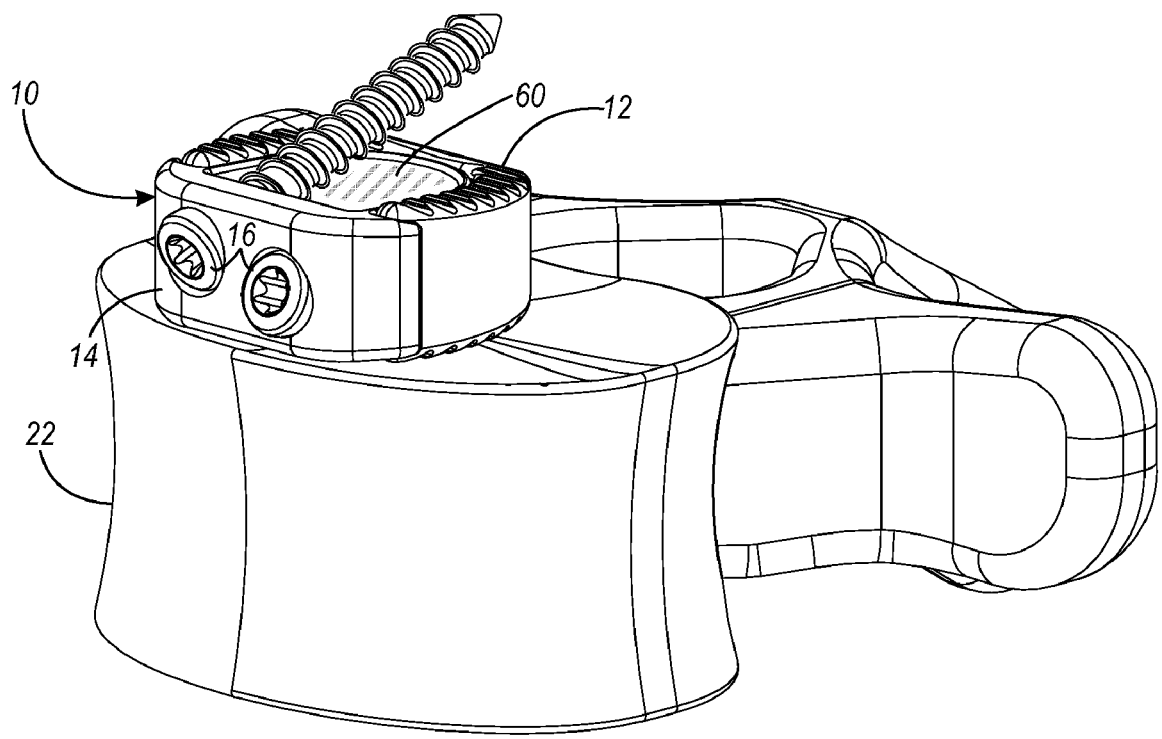
FIG. 10 is an isometric view similar to FIG. 9, but with the disc annulus and nucleus pulpous removed.
Figure 11:
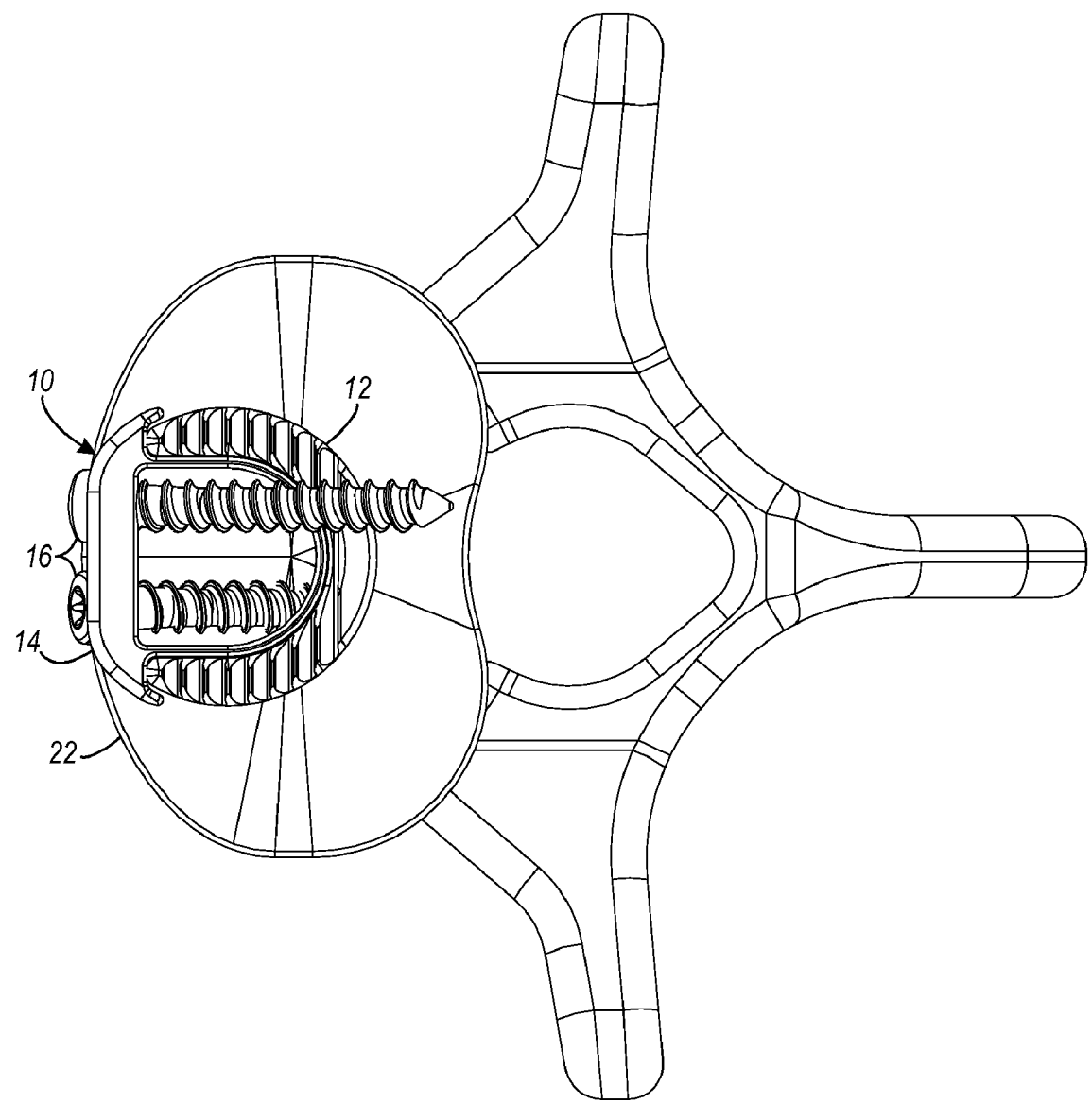
FIG. 11 is a top view of the interbody fusion device and vertebral body shown in FIG. 10.

FIG. 9 is an isometric view similar to FIG. 2, but with the vertebra 20 removed to illustrate how the interbody fusion device 10 is positioned relative to the vertebrae and disc annulus 24. FIG. 9 shows the disc annulus 24 with a portion removed to allow the interbody fusion device 10 to be inserted. FIG. 9 also shows the remaining nucleus pulpous 26 surrounding the interbody fusion device 10. FIG. 10 is an isometric view similar to FIG. 9, but with the disc annulus 24 and nucleus pulpous 26 removed to further illustrate how the interbody fusion device 10 is positioned relative to the vertebrae and disc annulus 24. FIGS. 9 and 10 also include shading, which represents fusion material 60, described above. FIG. 11 is a top view of the interbody fusion device 10 and vertebral body shown in FIG. 10. Note that, for clarity, the material 60 is not shown in FIG. 11.

Following is an example of how a interbody fusion device of the present invention may be used in an ALIF spinal fusion procedure. As described above, a window is cut in the anterior side of the disc annulus 24 (FIG. 9) to allow an interbody fusion device to be inserted. Next, the nucleus pulposus 26 is cleaned out to provide room for the interbody fusion device. Next, a load bearing device 12 of the desired size (e.g., having a height to get the desired spacing between the vertebrae) is inserted between the end plates of the adjacent vertebrae using the appropriate instrumentation. During these procedures, the retention device 14 can be prepared with a desire material 60 placed in the hollow body 46. Once the surgeon is satisfied that the load bearing device is in the ideal position, the retention device 14 is inserted into the load bearing device 12, with the tongue 36 and groove 32 guiding the retention device 14. Note that, because the height of the retention device is less than the height of the load bearing device, the retention device 14 can slide into the load bearing device 12 without interfering with the relative placement of the load bearing device 12 and the end plates of the adjacent vertebrae. Also, the retention device 14 is stress shielded and is not axial loaded by the vertebrae. Once the retention device is in place, the bone screws 16 can be installed through the openings 48 and into the vertebrae. As the bone screws 16 are tightened, the vertebrae will compress vertebral bodies 20 and 22 onto the load bearing member 12, which will help facilitate fusion. Also, since the bone screws 16 secure the retention device 14, and do not directly secure the load bearing device 12, the bone screws will not tend to cause the interbody fusion device 10 to migrate. If desired, an anti-backout mechanism (such as the set screw 50 shown in FIG. 7) can be used to prevent the bone screws 16 from loosening.

The interbody fusion device of the present invention can be made from any desired materials. In one example, the load bearing device is made from PEEK® (or a similar material), bone, metal, or any other structural substitute. In one example, the retention device is made from PEEK® (or a similar material), bone, metal, or any other structural substitute. If the components of the interbody fusion device are radio-lucent (such as with PEEK®), then doctors will be able monitor the fusion process better with X-rays.

An interbody fusion device of the present invention may be configured to any desired size or shape. In one example, load bearing devices can be provided in multiple thicknesses, allowing a surgeon to select a desired size (e.g., 10.5 mm, 12.5 mm, 14.5 mm, 16.5 mm, 1.5 mm, etc.). In the examples shown in the figures, the load bearing device has about 6° of lordosis (e.g., see FIG. 6). Of course any desired angle could be used.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A spinal fusion device comprising:
   a single U-shaped load bearing device configured to fit between two adjacent vertebrae and having an open end configured to receive a retention device;
   a retention device configured to be secured to at least one of the adjacent vertebrae to prevent migration of the load bearing device, wherein the retention device has a height that is less than the height of the fusion bearing device, wherein the retention device is oval-shaped having a front portion and a rear portion that together form a hollow center portion adapted to receive a material to enhance spinal fusion and wherein the U-shaped load bearing device and the retention device fit together to form a generally round profile that fits within a vertebral body; and
   two or more fastening devices for securing the retention device to at least one of the adjacent vertebrae, wherein the retention device includes bores for receiving the fastening devices, wherein a first bore is generally angled toward the top of the fusion device so that a first fastener is configured to contact an upper vertebral body when inserted through the first bore and wherein a second bore is generally angled toward the bottom of the fusion device so that a second fastener is configured to contact a lower vertebral body when the second fastener is inserted through the second bore.

2. The spinal fusion device of claim 1, wherein the retention device generally conforms to the contour of the adjacent vertebrae.

3. The spinal fusion device of claim 1, wherein each of the two or more fastening devices are inserted through an aperture formed in the retention device.

4. The spinal fusion device of claim 1, wherein the two or more fastening devices are bone screws.

5. The spinal fusion device of claim 1, wherein the U-shaped load bearing device and the retention device have a mating tongue and groove to limit relative motion between the fusion bearing device and the retention device.

6. The spinal fusion device of claim 1, further comprising an anti-backout mechanism coupled to the one or more fasteners to prevent fastener migration.

7. A method of fusing adjacent vertebrae: providing an interbody fusion device; inserting the interbody fusion device between two adjacent vertebrae; providing a retention device configured to fit within the interbody fusion device; sliding the retention device into the interbody fusion device; and securing the retention device to at least one of the adjacent vertebrae; wherein the spinal fusion device comprises: a single U-shaped load bearing device configured to fit between two adjacent vertebrae and having an open end configured to receive a retention device; a retention device configured to be secured to at least one of the adjacent vertebrae to prevent migration of the load bearing device, wherein the retention device has a height that is less than the height of the fusion bearing device, wherein the retention device is oval-shaped having a front portion and a rear portion that together form a hollow center portion adapted to receive a material to enhance spinal fusion and wherein the U-shaped load bearing device and the retention device fit together to form a generally round profile that fits within a vertebral body and two or more fastening devices for securing the retention device to at least one of the adjacent vertebrae, wherein the retention device includes bores for receiving the fastening devices, wherein a first bore is generally angled toward the top of the fusion device so that a first fastener is configured to contact an upper vertebral body when inserted through the first bore and wherein a second bore is generally angled toward the bottom of the fusion device so that a second fastener is configured to contact a lower vertebral body when the second fastener is inserted through the second bore.

8. A method of fusing adjacent vertebrae comprising: inserting an interbody fusion device between two adjacent vertebrae, the interbody fusion device being configured to bear against opposing end plates of the two adjacent vertebrae, the interbody fusion device having an open end; and preparing the end plates of the vertebrae for fusion; wherein the spinal fusion device comprises: a single U-shaped load bearing device configured to fit between two adjacent vertebrae and having an open end configured to receive a retention device; a retention device configured to be secured to at least one of the adjacent vertebrae to prevent migration of the load bearing device, wherein the retention device has a height that is less than the height of the fusion bearing device, wherein the retention device is oval-shaped having a front portion and a rear portion that together form a hollow center portion adapted to receive a material to enhance spinal fusion and wherein the U-shaped load bearing device and the retention device fit together to form a generally round profile that fits within a vertebral body and two or more fastening devices for securing the retention device to at least one of the adjacent vertebrae, wherein the retention device includes bores for receiving the fastening devices, wherein a first bore is generally angled toward the top of the fusion device so that a first fastener is configured to contact an upper vertebral body when inserted through the first bore and wherein a second bore is generally angled toward the bottom of the fusion device so that a second fastener is configured to contact a lower vertebral body when the second fastener is inserted through the second bore.

9. The method of claim 8, further comprising inserting fusion enhancing material between the end plates of the adjacent vertebrae.

10. The method of claim 8, wherein the end plates are prepared by disrupting the boney tissue of the end plates.

11. The method of claim 8, wherein the interbody fusion device is a U-shaped device.

* * * * *